United States Patent [19]

Jones et al.

[11] Patent Number: 4,898,969

[45] Date of Patent: Feb. 6, 1990

[54] TRANSESTERIFICATION OF ALKOXYESTERS

[75] Inventors: Glenn C. Jones; William D. Nottingham, both of Kingsport, Tenn.

[73] Assignee: Eastman Kodak Company, Rochester, N.Y.

[21] Appl. No.: 179,167

[22] Filed: Apr. 8, 1988

[51] Int. Cl.$^4$ .............................................. C07C 69/66
[52] U.S. Cl. ................................................... 560/187
[58] Field of Search ......................................... 560/187

[56] References Cited

U.S. PATENT DOCUMENTS 2,504,151  4/1950  Rehberg et al. ..................... 560/187
4,614,613  9/1986  Fikentscher et al. ............... 548/964

OTHER PUBLICATIONS

Mori et al., *Tetrahedron*, vol. 42, pp. 4685–4689 (1986).
Nie et al., Chemical Abstracts, vol. 107, No. 217895H (1987).
"Titanate-Mediated, Transesterifications With Functionalized Substrates", Seebach, et al., Synthesis Communications, pp. 138–141 (Feb., 1982).

*Primary Examiner*—Bruce Gray
*Attorney, Agent, or Firm*—S. E. Reiter; William P. Heath, Jr.

[57] ABSTRACT

Method for the highly selective transesterification of alkyl 3-alkoxypropionates, as well as several novel alkoxypropionate compounds, are provided. Transesterification catalyzed by titanium alkoxides or tin compounds does not catalyze the Michael reaction, and therefore, provide highly selective transesterification reactions of these reactive materials.

11 Claims, No Drawings

TRANSESTERIFICATION OF ALKOXYESTERS

This invention relates to catalysts useful for the transesterification of alkoxyesters as well as methods for carrying out such transesterification reactions.

BACKGROUND

A variety of unsymmetrically substituted alkyl 3-alkoxypropionates can be prepared by transesterification of identically substituted alkyl 3-alkoxypropionates. Unfortunately, the terminal alkyl moieties tend to scramble when known transesterification catalysts such alkali metal alkoxides, sulfuric acid and the like are used, apparently by promoting the reverse Michael reaction of the alkyl 3-alkoxypropionates. In addition, such catalysts produce other undesirable side products, presumably derived from the products of the reverse Michael reaction of the alkyl 3-alkoxypropionates. Other catalysts known to have transesterification activity do not produce by-products—because they are essentially unreactive with the alkoxyesters employed in the practice of the present invention. Thus, neither transesterification nor by-product formation occurs.

U.S. Pat. No. 4,614,613 (assigned to BASF Aktiengesellschaft) discloses the use of titanium (IV) or tin (V) compounds which are soluble in organic medium for transesterification of β-N-aziridinopropionates of lower alcohols with relatively high boiling alcohols or polyalcohols. This reference is specific to the transesterification of β-N-aziridinopropionates and addresses the problem of side reactions such as polymerization of the three-membered aziridine ring.

The specific compounds which are the subject of the '613 disclosure are subject to many side reactions and process constraints as a result of the presence of the aziridino moiety as part of the reactive molecule. The mono- and polymeric secondary and tertiary amine species present in the '613 reaction system are capable of interacting with the titanium and/or tin catalyst, thereby aiding the promotion of the desired reaction.

STATEMENT OF THE INVENTION

In accordance with the present invention, we have discovered that a defined class of titanium and tin compounds are effective catalysts for the highly selective transesterification of alkyl 3-alkoxypropionates. The resulting compounds are useful for a wide range of applications, e.g., as solvents for use in coating applications, as coalescing agents, as plasticizers, and the like.

DETAILED DESCRIPTION OF THE INVENTION

In accordance with the present invention, there is provided a method for the transesterification of alkoxyesters which comprises contacting an alkoxyester with at least one alcohol in the presence of a titanium or tin catalyst under conditions suitable to produce a transesterified product. The invention method involves contacting:
(a) alkoxyesters having the structural formula:

wherein each R is independently selected from the group consisting of H and $C_1$–$C_{10}$ alkyl moieties, with the proviso that the total number of carbon atoms for all R groups does not exceed 10, and each R' is independently selected from the group consisting of $C_1$–$C_{10}$ alkyl moieties with
(b) at least one alcohol having the structural formula:

$$R''—OH$$

wherein each R'' is selected from the group consisting of $C_1$–$C_{20}$ alkyl or cycloalkyl moieties, optionally substituted with one or more hydroxy- or alkoxymoieties in the presence of a catalyst selected from the group consisting of:
(i) a titanium alkoxide catalyst having the formula:

wherein each R''' is independently selected from the group consisting of $C_1$–$C_{10}$ alkyl moieties, and
(ii) a tin compound having the formula:

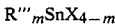

wherein R''' is as described above, X is oxygen, an alkyl or acyl radical of an organic acid having in the range of about 1 up to 10 carbon atoms, and m is an integer which varies in the range of 1 up to 3,
wherein said contacting is carried out for a time and at a temperature sufficient to produce the desired transesterification product having the structural formula:

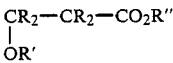

Preferred alkoxyesters are those wherein R is H, i.e., esters of propionic acid. Alkoxyesters contemplated within the scope of the present invention include:
ethyl 3-ethoxypropionate,
methyl 3-ethoxypropionate,
methyl 3-methoxypropionate,
propyl 3-propoxypropionate,
butyl 3-butoxypropionate,
isobutyl 3-isobutoxypropionate,
as well as mixtures of any two or more thereof.

Alcohols contemplated for use within the scope of the present invention include:
1-methoxy-2-propanol,
2-ethyl-1-hexanol,
methanol,
ethanol,
n-butanol,
isobutanol,
isopropanol,
n-propanol,
2,2,4-trimethylpentane-1,3-diol,
cyclohexanol,
2-(2-butoxyethoxy)ethanol,
glycerol,
pentaerythritol,
trimethylolpropane,
as well as mixtures of any two or more thereof.

Since the transesterification reaction involves reaction of one alcohol moiety with one alkoxyester moiety, these components can be mixed in essentially stoichiometric moieties. Of course, those of skill in the art recognize that an excess amount of either the alkoxyester or alcohol can be employed as reaction medium.

Titanium compounds contemplated for use in the practice of the present invention include titanium (IV) isopropoxide, titanium (IV) methoxide, titanium (IV) ethoxide, titanium (IV) propoxide, titanium (IV) butoxide, titanium (IV) isobutoxide, titanium (IV) 2-ethylhexoxide, and the like.

Tin compounds contemplated for use in the practice of the present invention include dibutyltin diacetate, dibutyltin oxide, dibutyltin dilaurate, and the like.

The invention transesterification reaction can be carried out at temperatures in the range of about 130° up to 210° C. Reaction times can vary in the range of about 1 up to about 24 hours. Pressure is not critical to the practice of the present invention and pressures from subatmospheric to superatmospheric up about 1,000 psig can be employed.

It is preferred that the invention transesterification process be carried out in an inert atmosphere, i.e., one which is substantially water free and having a low oxygen content, e.g., nitrogen, argon, and the like. It is desirable that oxygen levels be maintained below explosive limits.

Concentration of catalyst empoloyed in the practice of the present invention can vary widely, i.e., from about 0.01 up to 1.0 weight percent based on the weight of total reaction mixture. Preferably, for most efficient use of catalyst, desirable reaction rates and ease of product recovery, in the range of about 0.02 up to 0.2 weight percent catalyst, based on total weight of reaction mixture, will be employed.

Our invention will now be described in greater detail with reference to the following non-limiting examples.

EXAMPLES

All transesterification reactions were monitored by capillary gas chromatography (GC). All percentage values given in the examples are area percent.

EXAMPLE 1

Transesterification of Ethyl 3-Ethoxypropionate with 1-Methoxy-2-Propanol

A solution of 146 g (1.0 mole) ethyl 3-ethoxypropionate, 180 g (2.0 mole) 1-methoxy-2-propanol, and 2 g titanium (IV) isopropoxide was refluxed under a 15-inch Penn State packed column, and ethanol was removed as it was found. After 6 hours the reaction was 98.8% complete. Temperatures of 130°-140° C. were observed in the base of the column. By GC analysis no ethyl acrylate was observed in the ethanol distillate or in the crude product, 1-methoxy-2-propyl 3-ethoxypropionate. The crude product had only low levels of color.

EXAMPLE 2

Transesterification of Ethyl 3-Ethoxypropionate with 2-Ethylhexyl Alcohol

A solution of 268 g (2.06 moles) of 2-ethylhexanol, 442 g (3.03 moles) ethyl 3-ethoxypropionate, and 0.5 g titanium (IV) isopropoxide was refluxed under a 5-plate Oldershaw column, and ethanol was removed as it was formed. Over 1.5 hours the temperature in the base of the column rose from 155° C. to 210° C. GC analysis indicated the formation of only a single product. Distillate (97 g) came overhead at 76° C. to 163° C. The distillate had the following composition: 93.2 g ethanol, 0.3 g ethyl acrylate, 1.3 g water, and 2.1 g ethyl 3-ethoxypropionate. The product was distilled at less than 1.0 torr, and the base temperature was less than 140° C. The low-boiler cut was 133 g ethyl 3-ethoxypropionate, 0.1 g ethyl acrylate, 3.4 g product, and 0.2 g unknowns. The product, 2-ethylhexyl 3-ethoxypropionate (461 g, 97% yield) had 99.2% assay, and its structure was established by its infrared and NMR spectra. There was 7 g of product in the 8-g residue.

EXAMPLE 3

Transesterification of Isobutyl 3-Isobutoxypropionate with Cyclohexyl Alcohol

Isobutyl 3-isobutoxypropionate (51 g, 0.25 moles), cyclohexyl alcohol (75 g, 0.75 moles), and 0.5 g, titanium (IV) isopropoxide were mixed together and heated to reflux (170° C.) under a 5-plate Oldershaw column. The isobutanol distillate was removed at 106° C. GC analysis indicated the formation of only a single product. The remaining reaction product was vacuum distilled at less than 1.0 torr and 85° C. To recover 55 g (96.5% yield) of cyclohexyl 3-isobutoxypropionate, >98% pure by GC. NMR confirmed the structure.

EXAMPLE 4

Transesterification of Methyl 3-Methoxypropionate with 2-Ethyl-1-Hexanol

Methyl 3-methoxypropionate (72 g, 0.5 moles), 2-ethyl-1-hexanol (97 g, 0.75 moles), and 0.5 g titanium (IV) isopropoxide were mixed together and heated to reflux (180° C.) under a 5-plate Oldershaw column. The methanol distillate was removed at <70° C. GC analysis indicated the formation of only a single product. The remaining reaction product was vacuum distilled at 12 torr and 127° C. to recover 108 g (100% yield) of 2-ethyl-1-hexyl 3-methoxypropionate, 99% pure by GC. NMR confirmed the structure.

EXAMPLE 5

Transesterification of Ethyl 3-Ethoxypropionate with 2-(2-Butoxyethoxy)Ethanol

A mixture of 88% methyl 3-ethoxypropionate and 12% ethyl 3-ethoxypropionate (121 g, 1.0 mole), 2-(2-butoxyethoxy)ethanol (81 g, 0.5 moles) and 0.5 g titanium (IV) isopropoxide were heated to reflux (190° C.) under a 5-plate Oldershaw column. The methanol/ethanol distillate was removed at 68°-80° C. GC analysis indicated the formation of only a single product. The remaining reaction product was vacuum distilled at less than 1.0 torr and 110° C. To recover 125 g (95.4% yield) of 2-(2-butoxyethoxy)ethyl 3-ethoxypropionate, 97% pure by GC. NMR confirmed the structure.

EXAMPLE 6

Transesterification of Ethyl 3-Ethoxypropionate with 2,2,4-Trimethyl-1,3-Pentanediol (a) Preparation of pentanediol monoester:

Ethyl 3-ethoxypropionate (584 g, 4.0 moles), 2,2,4-trimethyl-1,3-pentanediol (292 g, 2.0 moles) and 2.0 g titanium (IV) isopropoxide were heated to reflux (170° C.) under a 5-plate column and ethanol distillate was removed at 78° C. The reaction was followed by GC and stopped when the ratio of monoester to di-ester reached 77/14. The product was then vacuum distilled through a 15-plate Oldershaw column at 1.0 torr and 102° C. to recover 290 g of 2,2,4-trimethyl-1,3-pentanediol mono 3-ethoxypropionate ester, >99% pure by GC. NMR supported this structure assignment with a ratio of 43% secondary ester and 57% primary ester indicated. Atmospheric boiling point is 264° C.

(b) Preparation of pentanediol diester:

Ethyl 3-ethoxypropionate (365 g, 2.5 moles), 2,2,4-trimethyl-1,3-pentanediol (TMPD) (146 g, 1.0 mole) and 1.0 g titanium (IV) isopropoxide were heated to reflux (170° C.) under a 5-plate column. The ethanol distillate wass removed at 78° C. The reaction was followed by gas chromatography (GC) and stopped when the TMPD content dropped to below 1% and the mono/di ratio was ¼. The reaction mixture was vacuum distilled through a 15-plate Oldershaw column at less than 1.0 torr and 162° C. to recover 175 g of 2,2,4-trimethyl-1,3-pentanediol di-3-ethoxypropionate ester, >98% pure by GC. NMR and IR support and confirm the structure. Atmospheric boiling point is 337° C.

EXAMPLE 7

Transesterification of Ethyl 3-Ethoxypropionate with Methyl Alcohol

To a 140° C. solution of 584 g (4.0 moles) ethyl 3-ethoxypropionate and 4 g titanium (IV) isopropoxide was added subsurface 546 g (17.0 moles) methyl alcohol over an 8-hour period. The reaction was refluxed under a 15-plate Oldershaw column and the low boiling alcohol distillate was removed at the same rate as the methanol addition. At the end of 8 hours, GC analysis indicated a single product was formed. The reaction mix contained 82.0% methyl 3-ethoxypropionate, 15.8% ethyl 3-ethoxyropionate, 0.9% methanol, 0.3% EtOH, and 1.0% high boilers. There were no acrylates (ethyl or methyl) or alkyl 3-methoxypropionates (ethyl or methyl) found in the product mixture.

EXAMPLE 8

Transesterification of Ethyl 3-Ethoxypropionate with n-Propyl Alcohol

To a 150° C. solution of 438 g (3.0 moles) ethyl 3-ethoxypropionate and 2.0 g titanium (IV) isopropoxide was added propyl alcohol below the surface. The alcohol distillate was removed through a 5-plate oldershaw column at such a rate that the temperature and reaction quantity remained constant. When the distillate temperature reached 93° C., the reaction was stopped. GC indicated a single product was formed. The reaction mixture contained 5.5% propanol, 2.0% ethyl 3-ethoxypropionate, 91.3% propyl 3-ethoxypropionate, and 1.3% others. There were no acrylates (propyl or ethyl) or alkyl 3-propoxypropionates (ethyl or propyl) present in the product mixture.

EXAMPLE 9

Transesterification of Ethyl 3-Ethoxypropionate with Cyclohexanol Using Dibutyltin Diacetate Catalyst Ethyl 3-ethoxypropionate (44 g, 0.3 moles), cyclohexanol (60 g, 0.6 moles) and 1.0 g dibutyltin diacetate were heated to reflux (160° C.) and the ethanol distillate was removed by distillation. GC analysis indicated the formation of only a single product. The reaction product was vacuum distilled at less than 1.0 torr and 89° C. to recover 55 g (91.7% yield) of cyclohexyl 3-ethoxypropionate, 99% pure by GC. NMR confirmed the structure.

EXAMPLE 10

Transesterification of Ethyl 3-Ethoxypropionate with Texanol ® Ester Alcohol

Texanol ® (435 g, 2.0 moles); Texanol ® ester alcohol is 2,2,4-trimethyl-1,3-pentanediol monoisobutyrate with the isobutyl ester being approximately 60% primary and 40% secondary), ethyl 3-ethoxypropinate (334 g, 2.3 moles), and titanium (IV) isopropoxide (2.0 g) were mixed together and heated to reflux (175°-195° C.) under a 5-plate Oldershaw column and ethanol was removed as it was formed. To control the temperature at less than 200° C., another 250 ml of ethyl 3-ethoxypropionate was added to the reaction mixture. After all ethanol was removed the reaction mixture was vacuum distilled through a 15-plate Oldershaw column at less than 1.0 torr and 122° C. to recover 380 g (60% yield) of >98% pure 2,2,4-trimethyl-1,3-pentanediol mixed isobutyrate and 3-ethoxypropionate esters. NMR and GC/MS analysis confirmed the structure. Atmospheric boiling point of these mixed esters is 308° C.

EXAMPLE 11

Transesterification of Ethyl 3-Ethoxypropionate with 1-Methoxy-2-Propanol Using Zinc Acetate Catalyst Ethyl 3-ethoxypropionate (146 g, 1.0 mole), 1-methoxy-2-propanol (180 g, 2.0 mole) and 0.9 g zinc acetate were refluxed under a 25-plate Oldershaw column arranged so as to remove ethanol as it is formed. After six hours reaction time there was no ethanol distillate. Gas chromatography of the reaction mixture indicated less than 1% of the product present.

The results of this experiment demonstrate that zinc acetate is ineffective as a transesterification catalyst for ethyl 3-ethoxypropionate.

EXAMPLE 12

Transesterification of Ethyl 3-Ethoxypropionate and Cyclohexanol Using Sulfuric Acid Catalyst Ethyl 3-ethoxypropionate (44 g, 0.3 moles), cyclohexanol (60 g, 0.6 moles) and 1.0 g concentrated sulfuric acid were heated to reflux for 30 minutes. GC/MS of the reaction mixture confirmed that three products were formed, ethyl acrylate 8%, cyclohexyl 3-ethoxypropionate 88%, and 2% ethyl 3-cyclohexoxypropionate.

The results of this experiment demonstrate that sulfuric acid gives a mixture of reaction products, compared to the very selective reaction obtained in accordance with the present invention (see Example 10).

EXAMPLE 13

Transesterification of Methyl 3-Methoxypropionate and 2-Ethyl-1-Hexanol Using Sodium Alkoxide Catalyst Methyl 3-methoxypropionate (72 g, 0.5 moles), 2-ethyl-1-hexanol (97 g, 0.75 moles) and 25% sodium methoxide in methanol (2.0 g) were mixed together and heated to reflux. GC/MS of the reaction mixture confirmed the presence of two products, 2-ethyl-1-hexyl 3-methoxypropionate (75%) and 2-ethyl-1-hexyl 3-(2-ethyl-1-hexoxy)propionate (25%).

The results of this experiment demonstrate that sodium alkoxide is not a selective catalyst for the transesterification of alkyl 3-alkoxypropionates.

The invention has been described in detail with particular reference to preferred embodiments thereof, but it will be understood that variations and modifications can be effected within the spirit and scope of the invention.

We claim:

1. A method for the transesterification of alkoxyesters having the structural formula:

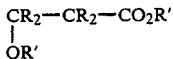

wherein each R is independently selected from the group consisting of H and $C_1$–$C_{10}$ alkyl moieties, with the provision that the total number of carbon atoms for all R groups does not exceed 10, and each R' is independently selected from the group consisting of $C_1$–$C_{10}$ alkyl moieties; said method comprising contacting said alkoxyester with at least one alcohol having the structural formula:

R''—OH wherein each R'' is selected from the group consisting of $C_1$–$C_{20}$ alkyl or cycloalkyl moieties, optionally substituted with one or more hydroxy- or alkoxy-moiety in the presence of a catalyst selected from the group consisting of:

(i) a titanium alkoxide catalyst having the formula:

wherein each R''' is independently selected from the group consisting of $C_1$–$C_{10}$ alkyl moieties, and (ii) a tin compound selected from the group consisting of:
dibutyltin diacetate,
dibutyltin oxide, and
dibutyltin dilaurate,
wherein said contacting is carried out for a time and at a temperature sufficient to produce the desired transesterification product having the structural formula:

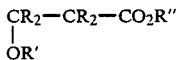

2. The method in accordance with claim 1 wherein all R-groups of said alkoxyester are H.

3. The method in accordance with claim 1 wherein said alkoxyester to be esterified is selected from the group consisting of:
ethyl 3-ethoxypropionate,
methyl 3-ethoxypropionate,
methyl 3-methoxypropionate,
propyl 3-propoxypropionate,
butyl 3-butoxypropionate,
isobutyl 3-isobutoxypropionate,
as well as mixtures of any two or more thereof.

4. The method in accordance with claim 1 wherein said alkoxyester is ethyl 3-ethoxypropionate.

5. The method in accordance with claim 1 wherein said alcohol is selected from the group consisting of:
1-methoxy-2-propanol,
2-ethyl-1-hexanol,
methanol,
ethanol,
n-butanol,
isobutanol,
isopropanol,
n-propanol,
2,2,4-trimethylpentane-1,3-diol,
cyclohexanol,
2-(2-butoxyethoxy)ethanol,
glycerol,
pentaerythritol,
trimethylolpropane,
as well as mixtures of any two or more thereof.

6. The method in accordance with claim 4 wherein said alcohol is methanol.

7. The method in accordance with claim 4 wherein said alcohol is n-propanol.

8. The method in accordance with claim 4 wherein said alcohol is 2,2,4-trimethylpentane-1,3-diol.

9. The method in accordance with claim 1 wherein said titanium alkoxide is selected from the group consisting of:
titanium (IV) isopropoxide,
titanium (IV) methoxide,
titanium (IV) ethoxide,
titanium (IV) propoxide,
titanium (IV) butoxide,
titanium (IV) isobutoxide, and
titanium (IV) 2-ethylhexoxide.

10. The method in accordance with claim 1 wherein said titanium alkoxide is titanium (IV) isopropoxide.

11. The method in accordance with claim 1 wherein said contacting is carried out at a temperature in the range of about 130° up to 210° C., for a time in the range of about 1 up to 24 hours.

* * * * *